(12) United States Patent
Gregory et al.

(10) Patent No.: US 8,068,666 B2
(45) Date of Patent: Nov. 29, 2011

(54) METHOD FOR READING TEST STRIPS

(75) Inventors: Walter Jay Gregory, Churchville, PA (US); William Harrison Stapelkamp, Delran, NJ (US)

(73) Assignee: Rohm and Haas Company, Philadelphia, PA (US)

( * ) Notice: Subject to any disclaimer, the term of this patent is extended or adjusted under 35 U.S.C. 154(b) by 881 days.

(21) Appl. No.: 12/074,823

(22) Filed: Mar. 6, 2008

(65) Prior Publication Data

US 2008/0219499 A1    Sep. 11, 2008

Related U.S. Application Data

(60) Provisional application No. 60/906,007, filed on Mar. 9, 2007.

(51) Int. Cl.
| | |
|---|---|
| G06K 9/00 | (2006.01) |
| G06K 9/46 | (2006.01) |
| G06K 9/66 | (2006.01) |
| G01N 21/00 | (2006.01) |
| G01N 21/75 | (2006.01) |
| G01N 21/77 | (2006.01) |

(52) U.S. Cl. ........ 382/162; 382/100; 382/128; 382/190; 382/195; 422/82.05; 436/164; 436/169

(58) Field of Classification Search ................. 382/100, 382/128, 162, 190, 195; 422/55, 56, 82.05; 436/164, 169
See application file for complete search history.

(56) References Cited

U.S. PATENT DOCUMENTS

| | | | |
|---|---|---|---|
| 5,323,473 A | 6/1994 | Lau | |
| 5,408,535 A | 4/1995 | Howard | |
| 5,754,448 A | 5/1998 | Edge et al. | |
| 6,197,522 B1 | 3/2001 | Keller | |
| 6,249,593 B1 | 6/2001 | Chu | |
| 6,315,866 B1 * | 11/2001 | Sanchez | 162/168.2 |
| 6,432,052 B1 | 8/2002 | Yao et al. | |
| 2002/0081233 A1 | 6/2002 | Lappe | |
| 2002/0132363 A1 * | 9/2002 | Rehm | 436/164 |
| 2003/0040128 A1 | 2/2003 | Meador | |
| 2004/0125998 A1 | 7/2004 | Wang | |

(Continued)

FOREIGN PATENT DOCUMENTS

EP    1416275    5/2004

(Continued)

OTHER PUBLICATIONS

Perkin-Elmer Co., "Geliance Gel and Chemi Imaging Systems" http://las.perkinelmer.com/Catalog/FamilyPage.htm?CategoryID=Geliance+Gel+and+Chemi+Imaging+Systems, May 30, 2008.

(Continued)

*Primary Examiner* — Bernard Krasnic
(74) *Attorney, Agent, or Firm* — Carl P. Hemenway

(57) ABSTRACT

There is provided a method for identifying the color intensities of red lines on a white test strip. The method comprises the following steps:

(A) attaching the white test strip to a card that is larger and darker than the white test strip, (B) scanning the card with the attached white test strip, (C) creating a digital image of the card, in which each pixel in the digital image has a Red value, a Green value, and a Blue value, (D) using the digital image to calculate a color intensity for each red line on the white test strip.

7 Claims, 1 Drawing Sheet

U.S. PATENT DOCUMENTS

| | | |
|---|---|---|
| 2004/0131238 A1 | 7/2004 | Wang |
| 2005/0129572 A1* | 6/2005 | Schulman et al. ............. 422/56 |
| 2006/0110283 A1* | 5/2006 | Fish .............................. 422/52 |
| 2008/0219499 A1 | 9/2008 | Gregory |

FOREIGN PATENT DOCUMENTS

| | | |
|---|---|---|
| JP | 6118000 | 4/1994 |
| JP | 10-274653 | 10/1998 |
| JP | 2001-242152 | 9/2001 |
| WO | WO 2004044560 A1 * | 5/2004 |

OTHER PUBLICATIONS

Moon, et al., "Optimal Edge-Based Shape Detection", IEEE Transactions on Image Processing, vol. 11/No. 11, pp. 1209-1226, Nov. 2002.

* cited by examiner

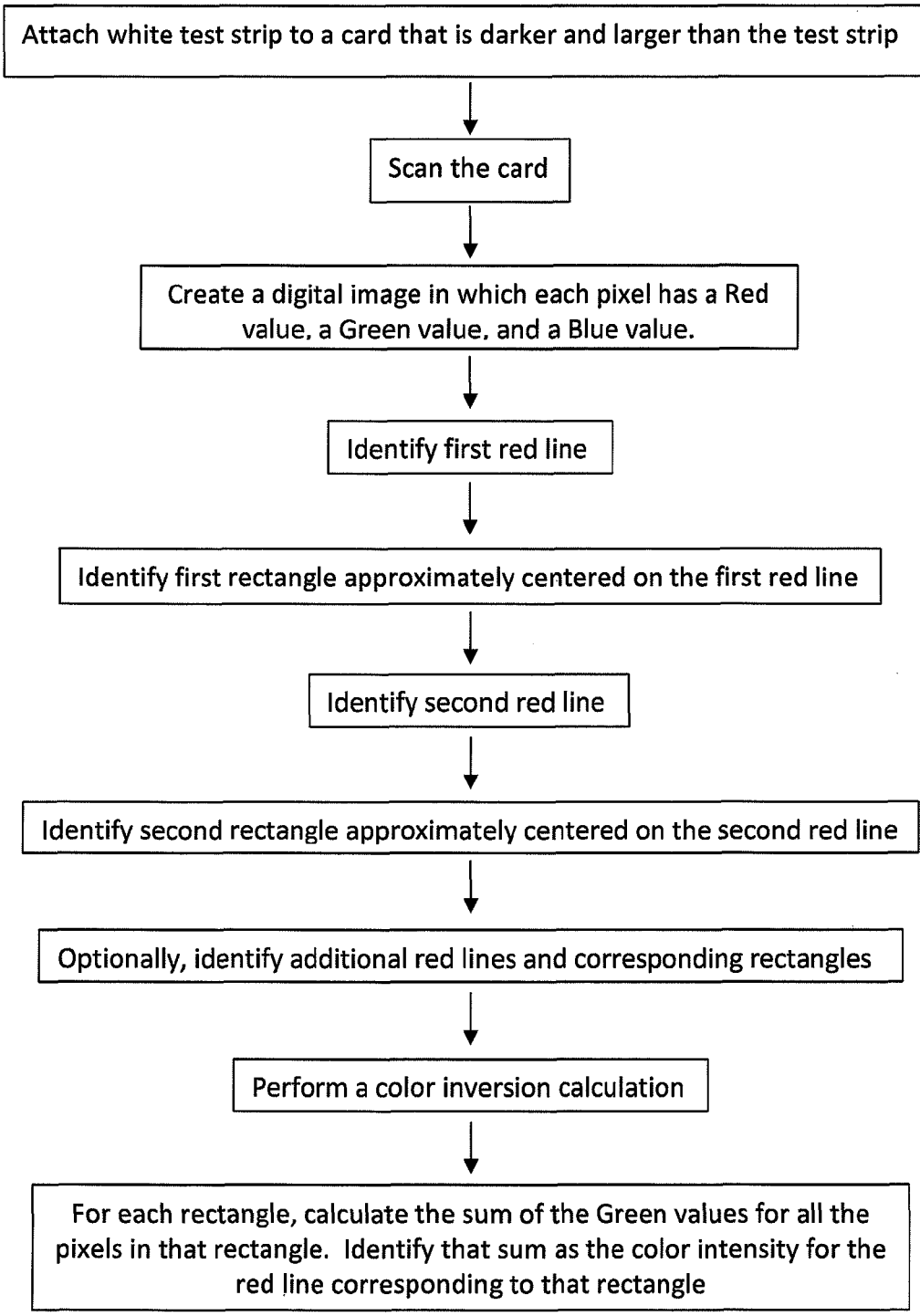

METHOD FOR READING TEST STRIPS

CROSS-REFERENCE TO RELATED APPLICATIONS

This application claims the benefit of priority under 35 U.S.C. §119(e) of U.S. Provisional Patent Application No. 60/906,007 filed on Mar. 9, 2007.

BACKGROUND OF THE INVENTION

It is often desired to quantitatively assess the intensities of the color of red lines on a white test strip. For example, US Patent Publication 2004/0131238 describes a method of assessing the color intensity of colored lines on white test strips by analyzing one or more individual scan lines taken in the direction of the long dimension of the test strip, so, if it is desired to use the data from multiple scan lines, either the long dimension of the sample must have been oriented perfectly in parallel to the direction of the scan, or else the data analysis needs to be extremely complicated. It is desired to provide a method of analyzing the intensities of the colors of red lines on a white test strip that involves relatively simple calculations and that is not affected by variations in the angle between the long axis of the test strip and the direction of the scan.

BRIEF SUMMARY OF THE INVENTION

In one aspect of the present invention, there is provided a method for identifying the color intensities of red lines on a white test strip, comprising the steps of
(A) attaching said white test strip to a card that is larger and darker than said white test strip,
(B) scanning said card with said attached white test strip,
(C) creating a digital image of said card, wherein each pixel in said digital image has a Red value, a Green value, and a Blue value,
(D) using said digital image to calculate a color intensity for each red line on said white test strip.

BRIEF DESCRIPTION OF THE DRAWINGS

The FIGURE is a flowchart identifying an embodiment of the present invention.

DETAILED DESCRIPTION OF THE INVENTION

As used herein a strip is an object that is relatively thin and is longer than it is wide. In some embodiments, suitable strips have thickness of 1 mm or less; or 0.5 mm or less. The ratio of length to width of a test strip is 1.5 or more. A test strip will be considered herein to be white if it would be judged to be white in color by most observers; test strips are suitably white if they are any shade of white, including such shades, for example, as cream, eggshell, or any other shade normally considered white.

The direction parallel to the long dimension of a strip is known herein as the "vertical" direction, and the direction parallel to the short dimension of a strip is known herein as the "horizontal" direction. That is, the size of the strip in the vertical direction is the length of the strip, and the size of the strip in the horizontal direction is the width of the strip. The edges of a strip that run in the vertical direction are known herein as vertical edges, and the other edges are known herein as horizontal edges.

A strip is considered herein to be a pre-test strip if it contains one or more test lines. A test line is a region containing assay material. A test line covers a region that stretches in the horizontal direction from one vertical edge of the pre-test strip to the other vertical edge. A test line has width (i.e., the size of the test line measured in the vertical direction) that is much smaller than the length of the pre-test strip. In some embodiments, the ratio of the width of a test line to the length of the pre-test strip is 0.2 or less; or 0.1 or less; or 0.03 or less; or 0.01 or less.

An assay material is a material that is sensitive to a particular subject material. That is, the assay material that is contained in or on a pre-test strip is not visible, but the assay material is capable of forming a colored material when contacted with a particular subject material. That is, the pre-test strip initially appears white all over, and after the pre-test strip is brought into contact with that particular subject material, the test line appears to have a color. In some embodiments, one or more test lines appears red. In some embodiments, each test line that appears to have a color appears red. A pre-test strip may have plural test lines, and each test line may be sensitive to a different subject material. It is contemplated that each test line will be separated from every other test line on the pre-test strip. In some embodiments, the ratio of the distance between two test lines to the average width of the test lines on that pre-test strip is 1 or higher, or 2 or higher, or 5 or higher.

A pre-test strip may be brought into contact with one or more subject materials in any way. For example, in some embodiments, a solution may be identified that may contain one or more subject materials.

After a pre-test strip has been brought into contact with a solution, the strip is known herein as a test strip. It is contemplated that a test line on the test strip will appear white if the solution did not contain the subject material to which that test line was sensitive. It is further contemplated that a test line on the test strip will appear colored if the solution did contain the subject material to which that test line was sensitive, and the color observed on that test line will have higher intensity, the greater the concentration in the solution of the subject material to which that test line was sensitive.

Pre-test strips may be made of any material. Some suitable pre-test strips are made of porous material (such as, for example, paper or cardboard) or of non-porous material such as, for example, polymeric film.

In some embodiments, the width of pre-test strip is 2 mm or more, or 5 mm or more, or 10 mm or more. Independently, in some embodiments, the length of the pre-test strip is 100 mm or less, or 75 mm or less, or 50 mm or less.

It is contemplated to use a solution of interest that may or may not contain a particular subject material (as used herein, "analyte" is a synonym for subject material). It is desired to determine what concentration, if any, of the analyte is present in the solution of interest.

One approach to determining the concentration of analyte in the solution of interest is to first add one or more further reagents to the solution of interest, optionally also diluting the solution of interest. In some embodiments, such addition of further reagents produces a testing solution that contains a reference material and a subject material. In some of such embodiments, (herein called "RS" embodiments) it is contemplated that the resulting solution is brought into contact with a particular type of pre-test strip. This particular pre-test strip has at least two test lines, one of which (the "reference line") is sensitive to the reference material and one of which (the "subject line") is sensitive to the subject material.

In RS embodiments, when the solution is contacted with such a pre-test strip to produce a test strip, the reference line will be colored if reference material was present in the solution, and the color intensity of the reference line will be greater, the higher the concentration that was present of reference material in the solution. Similarly, the subject line will be colored if subject material was present in the solution, and the color intensity of the subject line will be greater, the higher the concentration that was present of subject material in the solution.

It is contemplated that, in RS embodiments, the analyte, the further reagents, the optional dilution, and the pre-test strip can be chosen so that the ratio of the color intensity of the subject line to the color intensity of the reference line has a linear relation to the concentration of analyte in the solution of interest.

For example, in some embodiments, a reference material can be used that is capable of interacting with the analyte to form a chemical complex or of reacting with the analyte to form a reaction product or of binding with the analyte or any combination thereof. In such embodiments, the subject material is the chemical complex or the reaction product, while the reference material is the un-complexed or un-reacted additional reagent.

In some embodiments (herein called "chromatographic" embodiments), a solution containing analyte and, optionally, additional reagent or reagents, is placed in a container (such as, for example, a vial) to a depth that is small compared to the length of the pre-test strip. One end of the pre-test strip may then be placed in the container in a way that holds the pre-test strip upright or nearly upright. In such embodiments, it is contemplated that each test line on the pre-test strip is positioned on the pre-test strip above the level of the liquid solution in the bottom of the container. It is contemplated that a portion of the solution will come into contact with most or all of the pre-test strip as the solution travels from the bottom of the pre-test strip to toward the top of the pre-test strip by a chromatographic process such as, for example, capillary action, thin layer chromatography, paper chromatography, other chromatographic process, or a combination thereof. It is contemplated that, as the solution comes into contact with a particular test line, if the solution contains the subject material to which that test line is sensitive, that test line will form a colored material.

In some chromatographic embodiments in which the solution contains a reference material and a subject material, a pre-test strip is used that is constructed so that the test line that is sensitive to reference material is below the test line that is sensitive to subject material. In such embodiments, the solution will contact the test line that is sensitive to reference material before it contacts the test line that is sensitive to subject material. Such embodiments are called herein "LRC" embodiments.

In some embodiments, an analyte in the present invention is a polymer. A "polymer," as used herein and as defined by F W Billmeyer, JR. in *Textbook of Polymer Science*, second edition, 1971, is a relatively large molecule made up of the reaction products of smaller chemical repeat units. Normally, polymers have 11 or more repeat units. Polymers may have structures that are linear, branched, star shaped, looped, hyperbranched, crosslinked, or a combination thereof; polymers may have a single type of repeat unit ("homopolymers") or they may have more than one type of repeat unit ("copolymers"). As used herein, a "copolymer" is a polymer that contains two or more different types of repeat unit. Copolymers may have the various types of repeat units arranged randomly, in sequence, in blocks, in other arrangements, or in any mixture or combination thereof. Chemicals that react with each other to form the repeat units of a polymer are known herein as "monomers," and a polymer is said herein to be made of "polymerized units" of the monomers that reacted to form the repeat units. The chemical reaction or reactions in which monomers react to become polymerized units of a polymer are known herein as "polymerizing" or "polymerization."

Polymer molecular weights can be measured by standard methods such as, for example, size exclusion chromatography or intrinsic viscosity. Generally, polymers have weight-average molecular weight (Mw) of 500 or more.

Some polymers that are suitable as analytes in the present invention have a detectable terminus selected from a chain transfer agent, an initiator (or fragment thereof), a group attached to the chain transfer agent, or another functional group. Such polymers are known herein as "DT" polymers. DT polymers are usefully described as being composed of a body polymer and one or more covalently attached detectable terminus. In some embodiments, such polymers are also water-soluble.

Some polymers that are suitable as the body polymer are, for example, polymers or copolymers of carboxylic acids, especially acrylate polymers and derivatives thereof. Some suitable acrylate polymers include, for example, polymers and copolymers made from monomers of ethylenically unsaturated monocarboxylic acids containing 3-5 carbon atoms per molecule, and ethylenically unsaturated dicarboxylic acids containing 4-8 carbon atoms per molecule, as well as their alkali metal and ammonium salts, and the anhydrides of the cis dicarboxylic acids. Examples of monocarboxylic acids include, but are not limited to: acrylic acid, methacrylic acid, vinylacetic acid, crotonic acid, and acryloxypropionic acid. Of these, acrylic acid and methacrylic acid are known, for example, to be suitable. Examples of suitable dicarboxylic monomers include, but are not limited to: maleic acid, itaconic acid, mesaconic acid, fumaric acid, citraconic acid, tetrahydrophthalic acid, tetrahydrophthalic anhydride, and maleic anhydride. Among the dicarboxylic monomers, maleic anhydride, for example, is known to be suitable.

The polymer suitable as the body polymer may additionally be composed of up to 70 percent by weight ("wt %") of acid-free monoethylenically unsaturated monomers, so long as the polymer remains water-soluble. Such other monomers include, but are not limited to: alkyl esters of acrylic or methacrylic acid, such as, for example, methyl acrylate, ethyl acrylate, butyl acrylate, methyl methacrylate, ethyl methacrylate, butyl methacrylate, and isobutyl methacrylate; hydroxyalkyl esters of acrylic or methacrylic acid, such as hydroxyethyl acrylate, hydroxypropyl acrylate, hydroxyethyl methacrylate, and hydroxypropyl methacrylate; other types of acrylates or methacrylates, such as 2-sulfoethyl(meth) acrylate, 3-sulfopropyl(meth)acrylate, 2-sulfatoethyl(meth) acrylate, dimethylaminoethyl acrylate and phosphoethyl methacrylate; acrylamides and alkyl-substituted acrylamides such as methacrylamide, t-butylacrylamide, N-t-butyl-acrylamide, N-methyl acrylamide, N,N-dimethylacrylamide, and 3-N,N-dimethylaminopropylacrylamide; acrylonitriles such as methacrylonitrile; allyl alcohol; allyl sulfonic acid; allyl phosphonic acid; vinylphosphonic acid; 2-vinylpyridene; 4-vinylpyridene; N-vinyl pyrrolidone; N-vinylformamide; N-vinylimidazole; N-acrylomorpholine; acrolein; ethylene glycol diacrylate; trimethylolpropane triacrylate; diallyl phthalate; vinyl acetate; styrene; vinylsulfonic acid, p-styrenesulfonic acid, and 2-acrylamido-2-methylpropanesulfonic acid; methallyl sulfonate and 1-allyloxy-2-hydroxypropyl sulfonate (COPS®); acrylamidoglycolic acid; and salts of the above, as appropriate.

In some embodiments, the body polymer is polyacrylic acid ("PAA"), polymaleic acid, or a copolymer of acrylic acid and one or more additional monomer.

Independently, some body polymers have number average molecular weight ("Mn") of 500 or more, or 1,000 or more, or 2,000 or more. Independently, some body polymers have number average molecular weight ("Mn") of 1,000,000 or less; or 500,000 or less; or 100,000 or less; or 50,000 or less, or 25,000 or less.

Also contemplated are embodiments in which a body polymer is used that has weight-average molecular weight of 1,000,000 to 30,000,000.

Any chain transfer agent useful in controlling the molecular weight of polymer compositions can be used as a detectable terminus in the present invention. Such chain transfer agents include, but are not limited to: mercaptans, phosphinates, phosphonates, sulfinic acids (such as phenylsulfinic acid and p-toluenesulfinic acid), and amine-thiols. Suitable phosphinates include those disclosed as compounds of formula I (col. 1) in U.S. Pat. No. 5,294,371 (Clubley, et al.) and those disclosed as compounds of formula III (col. 4) in U.S. Pat. No. 5,376,731 (Kerr, et al.), and suitable amine-thiols include the type disclosed in U.S. Pat. No. 5,298,585 (McCallum, et al.). In some embodiments, it is suitable to use cysteine ("CYS"), aminoethane thiol ("AET"), or phenylphosphinic acid ("PPA") as the chain transfer agent.

Any initiator or initiator fragment useful in initiating free radical addition polymerization can be used as a detectable terminus in the present invention. Such initiator or initiator fragments include, but are not limited to: peroxyesters, such as t-butyl-perbenzoate and t-amylperoxybenzoate; dialkylperoxides, such as dicumylperoxide; diacylperoxides, such as benzoyl peroxide; hydroperoxides, such as cumene hydroperoxide; azo compounds, such as 2-phenylazo-4-methoxy-2,4-dimethyl-valeronitrile, 2,2'-azobis-2-methyl-N-phenylpropionamidine dihydrochloride, 2,2'-azobis-2(N-(4-chlorophenyl)-2-methylpropionamidine)dihydrochloride, 2,2'-azobis(2-(5-methyl-2-imidazoline-2-yl)propane)dihydrochloride, and 2,2'-azobis(2-(2-imidazolin-2-yl)propane) dihydrochloride.

Among embodiments in which detectable terminus is a group attached to the chain transfer agent, the chain transfer agent of choice is an amine-thiol, especially CYS or AET. Groups which can be attached to such chain transfer agents are those which will react specifically with the desired group, but not with other portions of the polymer. When the chain transfer agent contains a pendant amine, it is preferred to attach amine-reactive groups to them as detectable terminus. Suitable amine-reactive groups include but are not limited to: 1-(dimethylamino)-5-naphthalenesulfonic acid and its halides ("dansyl"); 4-dimethylaminoazobenzene-4-sulfonic acid and its halides ("dabsyl"); 2,4,6-trinitro-benzenesulfonic acid and its salts ("TNT"); 3-benzoylquinoline-2-carboxaldehyde; 3-(2-furfoyl)quinoline-2-carboxaldehyde; 2,4-dinitrofluorobenzene (Sanger's reagent); and ninhydrin. In some embodiments, suitable groups include: daisyl, dabsyl, and TNT.

Some commercially available examples of suitable polymers with detectable terminus are OPTIDOSE™ 1000 (sodium salt of polycarboxylate), OPTIDOSE™ 2000 (modified polycarboxylate), OPTIDOSE™ 3100 (terpolymer of carboxylate, sulfonate, and nonionic monomers), and OPTIDOSE™ 4210 (polymaleic acid), available from Rohm and Haas Company.

In some embodiments, a solution is used that contains DT polymer and an additional polymer; the additional polymer is similar to or identical to the body polymer of the DT polymer, and the weight ratio of DT polymer to the additional polymer in the solution is known. It is contemplated that the present invention can be used to determine the concentration of DT polymer in the solution, and the amount of additional polymer in the solution can then be easily determined.

In some RS embodiments in which the analyte contains a DT polymer, a reference material is used that contains an antibody. In embodiments in which the reference material contains an antibody, the antibody may optionally be conjugated with a marker. It is contemplated that the antibody itself or the antibody conjugated with the marker is capable of forming a complex with the detectable terminus of a DT polymer. It is further contemplated that a molar excess of antibody or of antibody conjugated with marker be used in comparison to the detectable terminus sites of the DT polymer; thus the solution will have a mixture of (1) DT polymers complexed with antibody or with antibody conjugated with marker and (2) antibody or antibody conjugated with marker that is "free" (i.e., not complexed with DT polymer).

In such embodiments using DT polymer and antibody or antibody conjugated with marker, it is contemplated that the first test line will be the reference test line and will contain an assay material (the "reference assay material") capable of trapping the free antibody or antibody conjugated with marker but not capable of trapping the DT polymer complexed with antibody or with antibody conjugated with marker. Such a reference assay material may, for example, be based on immunoassay technology. It is further contemplated that the second test line will be a subject test line and will contain a subject assay material capable of trapping all antibody conjugated with markers, whether they are free or complexed. Such a subject assay material may be, for example, based on immunoassay technology. It is contemplated that the reference assay material and the subject assay material will be different materials, even in embodiments in which both are based on immunoassay technology.

In the practice of the present invention, a test strip is attached to a card that is larger and darker than the test strip. Some suitable cards are, for example, rectangular and are larger than the test strip. "Darker" herein means that the card is any color that is easily distinguished from white. In some embodiments, the color of the card has significantly higher Blue value than the color of the pre-test strip. Suitable cards may be flexible or may be stiff enough to support themselves when held at one edge. Suitable cards may be, for example, 3 mm thick or less, or 2 mm thick or less, or 1 mm thick or less. Independently, some suitable cards may be, for example, made of cardboard. Independently, in some embodiments, a card is used that has a ratio of the width of the card to the width of the test strip of 1.5 or higher, or 3 or higher, or 5 or higher. Independently, in some embodiments, a card is used that has a ratio of the length of the card to the length of the test strip of 1.1 or higher, or 1.2 or higher. Independently, a card is used that has a ratio of length to width of 1.2 or higher, or 1.5 or higher, or 2 or higher.

It is contemplated that a flat side of the test strip will be attached to a flat side of the card so that the colored line or lines on the test strip are visible. It is contemplated that the length of the test strip will be parallel or approximately parallel to the length of the card, and that the test strip will be centered or approximately centered on the card in the horizontal direction. The test strip may be attached to the card using any type of fastening system that does not significantly distort or discolor the test strip, such as, for example, tape, glue, or other adhesive. If tape is used, clear tape is suitable.

In the practice of the present invention, the card with the attached test strip is optically scanned to form a digital image the card with the attached test strip. The digital image will have assigned to each pixel a Red value, a Green value, and a Blue value.

Any scanner and accompanying electronic circuits (including software) that can produce such a digital image is suitable. In some embodiments, a portable scanner designed for scanning business cards is used.

In some embodiments, the scanner is calibrated to the pre-test strip as follows. A pre-test strip (which appears white all over) is scanned, the average responses of the Red, Green, and Blue detectors over the area of the pre-test strip are each calculated, and the average response of each detector is set to a value of 256. In embodiments in which such calibrations are performed, it is contemplated that such calibrations will be performed periodically over time, so that the white areas of each pre-test strip yield Red, Green, and Blue values each of 256 or close to 256.

In the practice of the present invention, the digital image is used to calculate the color intensity of each colored line on the test strip.

The practice of the present invention is especially useful when each colored line on the test strip is red.

In some embodiments, images (herein called "locator" images) are printed on the pre-test strip, and these images remain visible after the pre-test strip becomes a test strip. Such images are a known distance from each test line and assist the process of finding the test lines in the digital image of the card with the attached test strip. Independently, in some embodiments, one or more guide marks may be made on the card prior to attaching the test strip, to aid in positioning the test strip on the card.

In some embodiments, the process of calculating the color intensity of a first red test line includes the following steps. First the red line is identified. That is, some portion of the pixels that correspond to that red line is identified. One method, for example, of identifying the first red line is to examine each pixel in a vertical line starting from the bottom of the card. It is contemplated that the pixels that correspond to a vertical line in the digital image may not form a line that is exactly parallel with the vertical edges of the test strip, if the direction of the scan was not exactly parallel to the vertical edges of the card. Still, it is contemplated to examine the pixels in a line that is recorded in the digital image as vertical. For example the Red and Green values can be examined, and it is contemplated that in a red line (and only in a red line) the ratio of the Red value to the Green value (the R/G ratio) is greater than 1.2. Therefore, a group of consecutive pixels in that vertical line with R/G ratio greater than 1.2 identifies a red line. The center pixel in that group of consecutive pixels is characterized by the vertical coordinate (YR1) in the digital image. In the group of consecutive pixels, the two pixels farthest from the center pixel will have vertical coordinates of YR1T and YR1B. The vertical size of the first red line is thus, in number of pixels, the absolute value of YR1T−YRTB.

If desired, the location of the locator image can be easily identified and the number of pixels in the vertical line between the locator image and the identified red line can be compared with the known distance between the locator image and the red lines. Such a comparison may, if desired, be used to aid in locating a red line or may act as a verification of the identification of a red line.

Next, pixels in a horizontal line (perpendicular to the direction of scan) are considered. As successive pixels farther from the vertical scan line mentioned above are considered, eventually, there will be a sudden increase of the Blue value, and the last pixel with the lower Blue value is considered to be the vertical edge of the test strip. The two vertical edges of the test strip can thus be determined, and they will have horizontal coordinates in the digital image of XR1L and XR1R. The horizontal center point of the first red line is considered to have horizontal coordinate of XR1=(½)*(XR1L+XR1R). The horizontal size of the first red line, in pixels, is the absolute value of XR1L−XR1R.

After a first red line is identified, a "first rectangle" can then be identified that corresponds to that first red line. A rectangle is considered to be a group of pixels in the digital image that, if marked (e.g., by a distinctive color) on a visible image of the digital image of the card, would appear as a rectangle that has sides perpendicular and parallel to the direction of scan. In the horizontal direction, the first rectangle will be exactly or approximately centered on the image of the test strip. The first rectangle has center point of the pixel with coordinates (XR1, YR1).

The first rectangle will have horizontal size that is smaller than the horizontal size of the first red line. In some embodiments, the ratio of the horizontal size of the first rectangle to the horizontal size of the first red line is 0.9 or smaller, or 0.8 or smaller, or 0.7 or smaller. Independently, in some embodiments, the ratio of the horizontal size of the first rectangle to the horizontal size of the first red line is 0.3 or larger, or 0.5 or larger.

The first rectangle will have vertical size that is larger than the vertical size of the first red line. In some embodiments, the ratio of the vertical size of the first rectangle to the vertical size of the first red line is 1.1 or larger, or 1.3 or larger, or 1.5 or larger. Independently, in some embodiments, the ratio of the vertical size of the first rectangle to the vertical size of the first red line is 5 or smaller, or 3 or smaller, or 2 or smaller.

For each additional red line on the test strip, a corresponding rectangle can be found. It is contemplated that, for the nth red line, the corresponding nth rectangle will be determined by the methods described above for the first red line and the corresponding first rectangle. It is further contemplated that the relationship of the location of the nth rectangle to the nth red line, the relationship of the horizontal size of the nth rectangle to the horizontal size of the nth red line, and the relationship of the vertical size of the nth rectangle to the vertical size of the nth red line, will all be the same as the relationships described above of the first rectangle to the first red line.

It is contemplated that every identified rectangle will have the same horizontal size as every other identified rectangle. In some embodiments, every identified rectangle will have the same vertical size as ever other identified rectangle.

In some embodiments, the color intensity of each red line is calculated by the following method. The digital image of the card is subjected to a color inversion calculation. Color inversion is a well known calculation and is readily available in most image-processing software programs. Within each identified rectangle, after the color inversion calculation, the pixels that fall outside of the red line will have Green values near zero; such pixels in the original test strip were white and thus had high Green values, Red values, and Blue values; and after color inversion, such pixels will have Green values, Red values, and Blue values of zero or nearly zero. Within each identified rectangle, the pixels of the red line will have significant Red values before the color inversion, which will be converted to Green values after the inversion.

After the color inversion, within each identified rectangle, the sum of all the Green values of all the pixels is calculated.

It is contemplated that the pixels outside the red line will contribute little or nothing to such a sum. This sum for the first rectangle is considered to be the color intensity of the first red line, and this sum for the first red line is herein labeled "CI1." This sum for the second rectangle is considered to be the color intensity of the second red line, and this sum for the second red line is herein labeled "CI2." In general, it is considered that this sum for the nth rectangle is considered to be the color intensity of the nth red line, and this sum for the nth rectangle is labeled herein "CIn."

The above methods of calculating color intensities may be used, for example, in test strips produced in LRC embodiments. In such embodiments, the first red line can be considered to be the test line closest to the liquid solution, and the second red line can be considered to be the test line other than the first red line that is closest to the liquid solution. In some of such embodiments, the first red line is the reference line and the second red line is the subject line. In such embodiments, it is contemplated that a linear relation exists between the concentration of analyte (herein labeled "CA") in the solution and the ratio R of CI2 to CI1 (that is, R=CI2/CI1).

A linear relation between CA and R means herein the following. Various solutions (N in number) of are prepared (labeled with a number "i" which runs from 1 to N), each with a specific analyte concentration (labeled CAi). Each solution is tested and analyzed as described above and value for R is calculated and recorded as Ri. The values for concentration and for R are arranged as data pairs (CAi, Ri), and a linear regression is performed to calculate the best-fit line CA=m*R+b. If the well-known statistical R-squared parameter of that best-fit line is 0.8 or better, a linear relation is said herein to exist between CA and R.

It is contemplated that, when a linear relation exists between CA and R, that relation will be in effect over a finite range of values of CA. It is further contemplated that if it is desired to analyze solutions in which CA is outside of the range over which the linear relation is in effect, the measurement could be made in a different way (for example, by using a different concentration of reference material) to alter the range of CA values over which the linear relation is in effect, so that the anticipated value of CA is within the range of values of CA over which the linear range is in effect.

In some embodiments, a linear relation between CA and R is in effect over a concentration from a minimum of CAMIN to a maximum concentration of CAMAX. In some embodiments, the ratio of CAMAX to CAMIN is 2 or higher; or 4 or higher; or 6 or higher.

In some embodiments, the solution containing analyte has concentration of analyte, by weight based on the weight of solution, of 0.1 ppm or more; or 0.2 ppm or more; or 0.5 ppm or more; or 1 ppm or more; or 2 ppm or more. Independently, in some embodiments, the solution containing analyte has concentration of analyte, by weight based on the weight of solution, of 50 ppm or less; or 30 ppm or less; or 15 ppm or less.

The methods of the present application may be used for a wide variety of purposes. One example of such a purpose is as follows. Water systems, such as, for example, cooling water systems, boilers, reverse osmosis units, evaporators, pools, washers, oil recovery processes, etc., are subject to formation of scale and corrosion on the inner surface. Addition of dispersant polymers (such as, for example, the polymers or copolymers of carboxylic acids described herein above) can aid in reducing the formation of scale or corrosion or both. The concentration of such polymers or copolymers in water systems is known to be subject to change over time, so it is desired to provide a method of analyzing the concentration of such polymers in water systems.

One method of analyzing the concentration of such polymers in water systems is to use as the dispersant polymer a polymer or copolymer carboxylic acid that has a detectable terminus as described herein above. It is also contemplated to use as the dispersant a blend of one or more polymers or copolymers of carboxylic acids without detectable terminus with one or more polymers or copolymers of carboxylic acids that do have detectable terminus.

In some embodiments in which a dispersant polymer is added to a water system, other materials may also be added to the water system. Such other materials include, for example, one or more of phosphates, zinc, azoles, phosphonates, biocides, other useful materials, and combinations thereof.

EXAMPLES

Test Procedure

In the following examples, the scanner used was and IRISCard™ Pro scanner by IRIS company. This is a self feeding business card scanner with 238 dots per centimeter (600 dots per inch) resolution, 24 bit color, and 11.8 cm by 30.5 cm (4.25 inch by 12 inch) adjustable scanning area.

Test strips were 0.64 cm×6.4 cm (0.25 inch by 2.5 inch). Cards were 5.1 cm by 8.9 cm (2 inch by 3.5 inch), colored gray.

Solutions of analyte were analyzed using an OPTIDOSE™ Test Kit available from Strategic Diagnostics, Inc. Following the instructions in the test kit, 50 microliter of analyte solution was added to the test tube, and then the supplied buffer solution was added up to the line labeled "5 ppm." 100 microliter of the resulting mixture was transferred to the reagent vial and the test strip was placed in the vial. After 10 minutes, the strip was removed and allowed to dry for 15 minutes. The strip was then taped to the gray card. Gray card was scanned and the image was analyzed as described herein above to produce the ratio R, with the added step that, within each identified rectangle, the ten pixels with the weakest red intensities were omitted from the process (performed after color inversion) of summing the Green values of all the pixels in that rectangle.

Example 1

OPTIDOSE™ 1000

Various solutions were prepared and tested using the test procedure described above. Each solution was OPTIDOSE™ 1000 in deionized water. The results were as follows, showing Concentration (Conc.) in ppm and the ratio of color intensity R.

| Conc. (ppm) | Ratio (R) |
| --- | --- |
| 2.1 | 0.45 |
| 2.1 | 0.45 |
| 2.1 | 0.46 |
| 3.3 | 0.58 |
| 3.3 | 0.58 |
| 3.3 | 0.59 |
| 4.6 | 0.75 |
| 4.6 | 0.76 |
| 4.6 | 0.77 |

| Conc. (ppm) | Ratio (R) |
|---|---|
| 5.5 | 0.82 |
| 5.5 | 0.82 |
| 5.5 | 0.81 |
| 6.5 | 0.92 |
| 6.5 | 0.91 |
| 6.5 | 0.92 |
| 7.4 | 0.96 |
| 7.4 | 0.95 |
| 7.4 | 0.94 |

| Conc. (ppm) | Ratio (R) |
|---|---|
| 8.4 | 1.03 |
| 8.4 | 1.04 |
| 8.4 | 1.02 |
| 9.7 | 1.23 |
| 9.7 | 1.23 |
| 9.7 | 1.22 |
| 11.6 | 1.41 |
| 11.6 | 1.41 |
| 11.6 | 1.41 |

The linear least squares best fit to these data is $CA=10.188*R-2.6557$, with R-squared value of 0.9888

Example 2

OPTIDOSE 2000

The procedures of Example 1 were used, except that the analyte was OPTIDOSE™ 2000.

| Conc. (ppm) | Ratio (R) |
|---|---|
| 2.8 | 0.47 |
| 2.8 | 0.47 |
| 2.8 | 0.47 |
| 4.2 | 0.59 |
| 4.2 | 0.59 |
| 4.2 | 0.58 |
| 5.4 | 0.69 |
| 5.4 | 0.69 |
| 5.4 | 0.69 |

| Conc. (ppm) | Ratio (R) |
|---|---|
| 6.4 | 0.81 |
| 6.4 | 0.79 |
| 6.4 | 0.77 |
| 6.4 | 0.79 |
| 6.4 | 0.81 |
| 6.4 | 0.79 |
| 6.4 | 0.80 |
| 6.4 | 0.80 |
| 6.4 | 0.80 |

| Conc. (ppm) | Ratio (R) |
|---|---|
| 6.4 | 0.81 |
| 8.0 | 0.95 |
| 8.0 | 0.95 |
| 8.0 | 0.95 |
| 9.5 | 0.98 |
| 9.5 | 0.98 |
| 9.5 | 0.98 |
| 10.6 | 1.23 |
| 10.6 | 1.22 |

| Conc. (ppm) | Ratio (R) |
|---|---|
| 10.6 | 1.23 |
| 11.6 | 1.24 |
| 11.6 | 1.24 |

| Conc. (ppm) | Ratio (R) |
|---|---|
| 11.6 | 1.23 |
| 12.8 | 1.41 |
| 12.8 | 1.41 |

| Conc. (ppm) | Ratio (R) |
|---|---|
| 12.8 | 1.41 |

The linear least squares best fit to these data is $CA=10.742*R-2.067$, with R-squared value of 0.9829.

Example 3

OPTIDOSE™ 3100

The procedures of Example 1 were used, except that the analyte was OPTIDOSE™ 3100.

| Conc. (ppm) | Ratio (R) |
|---|---|
| 2.1 | 0.22 |
| 2.1 | 0.25 |
| 2.1 | 0.22 |
| 3.2 | 0.32 |
| 3.2 | 0.33 |
| 3.2 | 0.34 |
| 4.1 | 0.45 |
| 4.1 | 0.44 |
| 4.1 | 0.45 |

| Conc. (ppm) | Ratio (R) |
|---|---|
| 5.2 | 0.57 |
| 5.2 | 0.60 |
| 5.2 | 0.58 |
| 6.2 | 0.66 |
| 6.2 | 0.65 |
| 6.2 | 0.66 |
| 7.3 | 0.69 |
| 7.3 | 0.69 |
| 7.3 | 0.70 |

| Conc. (ppm) | Ratio (R) |
|---|---|
| 8.3 | 0.80 |
| 8.3 | 0.80 |
| 8.3 | 0.81 |
| 9.4 | 0.84 |
| 9.4 | 0.84 |
| 9.4 | 0.83 |
| 10.4 | 0.95 |
| 10.4 | 0.94 |
| 10.4 | 0.95 |

The linear least squares best fit to these data is CA=11.7*R−0.9399, with R-squared value of 0.977.

Example 4

Reproducibility Studies

Various reproducibility studies were performed, the reproducibility of the test is excellent. For example, replicate solutions were prepared using OPTIDOSE™ 2000. On each day, one solution was made and was scanned ten times. The procedure was repeated on four days. 37 scans were made, in all. The solutions had 9.5 ppm of OPTIDOSE™ 2000. Overall, for all the measurements, the average Ratio R was 9.7, with a standard deviation of 0.48.

We claim:

1. A method for identifying color intensities of red lines on a white test strip, comprising the steps of
   (A) attaching said white test strip to a card that is larger and darker than said white test strip,
   (B) scanning said card with said attached white test strip,
   (C) creating a digital image of said card, wherein each pixel in said digital image has a Red value, a Green value, and a Blue value,
   (D) using said digital image to calculate a color intensity for each red line on said white test strip,
   wherein said step (D) is performed using a method comprising
   (a) identifying a first red line, and identifying a first rectangle corresponding to said first red line, wherein said first rectangle
      (i) is approximately or exactly centered on said test strip in a horizontal direction,
      (ii) is smaller than said test strip in the horizontal direction,
      (iii) extends above and below said first red line in a vertical direction,
   (b) identifying a second red line, and identifying a second rectangle corresponding to said second red line, wherein said second rectangle
      (i) is approximately or exactly centered on said test strip in the horizontal direction,
      (ii) is smaller than said test strip in the horizontal direction,
      (iii) extends above and below said second red line in the vertical direction,
   (c) optionally, repeating said step (b) for each additional red line to identify an additional rectangle corresponding to said additional red line,
   (d) performing a color inversion calculation, and
   (e) after performing said steps (a), (b), and (c), and (d), calculating a sum of the Green values of all the pixels within each rectangle, to produce a first sum of Green values corresponding to said first rectangle, a second sum of Green values corresponding to said second rectangle, and, optionally, an additional sum of Green values corresponding to each additional rectangle,
   wherein said first sum of Green values corresponding to said first rectangle is said color intensity of said first red line,
   wherein said second sum of Green values corresponding to said second rectangle is said color intensity of said second red line,
   and wherein said additional sum of Green values corresponding to each said additional rectangle is said color intensity of said additional red line to which said additional rectangle corresponds.

2. The method of claim 1, further comprising the step of calculating a ratio of said second sum of Green values to said first sum of Green values.

3. The method of claim 1, wherein said test strip is produced by a chromatographic process in which one end of a pre-test strip is placed into a solution, wherein said solution comprises an analyte and a complexing agent capable of forming a complex with said analyte, and wherein said pre-test strip comprises a line of a reference assay material capable of turning red on contact with free molecules of said complexing agent and a line of test assay material capable of turning red on contact with molecules of said complex of said analyte and said complexing agent.

4. The method of claim 3, wherein said analyte is a polymer.

5. The method of claim 4 wherein said polymer is a dispersant polymer.

6. The method of claim 5 wherein said dispersant polymer with one or more detectable terminus selected from chain transfer agents, initiators or fragments thereof, and groups attached to a chain transfer agent.

7. The method of claim 3, wherein said pre-test strip contains one or more printed image, wherein each printed image is a known distance from each of said line of reference assay material and from said line of test assay material.

* * * * *